United States Patent [19]
Dybdahl

[11] Patent Number: 5,894,080
[45] Date of Patent: Apr. 13, 1999

[54] USE OF A SAMPLING APPARATUS FOR CALIBRATING ELECTRONIC MASS/FLOW FRACTION METERS IN A PIPELINE

[76] Inventor: Bjørn Dybdahl, Lillesund Terrasse 4D N-5500, Haugesund, Norway

[21] Appl. No.: 08/765,129

[22] PCT Filed: Jun. 16, 1995

[86] PCT No.: PCT/NO95/00104

§ 371 Date: Dec. 23, 1996

§ 102(e) Date: Dec. 23, 1996

[87] PCT Pub. No.: WO96/00837

PCT Pub. Date: Jan. 11, 1996

[30] Foreign Application Priority Data

Jun. 29, 1994 [NO] Norway ................................ 942445

[51] Int. Cl.$^6$ .................................................. G01F 25/00
[52] U.S. Cl. ........................ 73/1.25; 73/1.16; 73/1.35
[58] Field of Search ............................ 73/1.02, 1.06, 73/1.25, 863.81, 863.82, 863.85, 863.86, 863.83, 1.16–1.36

[56] References Cited

U.S. PATENT DOCUMENTS

| | | | |
|---|---|---|---|
| 3,187,551 | 6/1965 | Hill. | |
| 3,455,143 | 7/1969 | Shamp | 73/1.24 |
| 4,094,187 | 6/1978 | Navarre, Jr. | 73/863.83 |
| 4,290,298 | 9/1981 | Severson | 73/1.16 |
| 4,341,107 | 7/1982 | Blair et al. | 73/1.34 |
| 5,161,417 | 11/1992 | Strong et al. | 73/863.86 |
| 5,259,239 | 11/1993 | Gaisford | 73/61.44 |
| 5,538,344 | 7/1996 | Dybdahl | 366/340 |
| 5,684,246 | 11/1997 | Korpi | 73/3 |

FOREIGN PATENT DOCUMENTS

| | | | |
|---|---|---|---|
| 235024 | 10/1991 | Japan | 73/1.16 |
| 2041035 | 9/1980 | United Kingdom. | |

Primary Examiner—Hezron Williams
Assistant Examiner—Nashmiya Fayyaz
Attorney, Agent, or Firm—Fulbright & Jaworski L.L.P.

[57] ABSTRACT

In order to eliminate heavy and expensive test separators on board offshore platforms, the invention proposes to use a sampling apparatus, which is designed, shaped and adapted to take fluid samples isokinetically from a mass flow containing a two or multi-phase fluid flowing in a pipeline. The pipeline is assigned calibratable electronic mass flow/fraction meters, the task thereof being to determine the produced amounts/share of the respective fractions (oil, gas, water/condensate, formation sand, etc.), and deliver data for such a determination to a computer. The sampling apparatus is coupled to the pipeline at a through-going hole for insertion/withdrawal of a probe having at least one orifice plate and being included in the sampling apparatus, as well as being adapted to be placed across substantially the complete internal diameter thereof and, following conclusion of sampling, to be withdrawn from the pipeline. Upon the withdrawal of the probe, the pipeline's insertion/withdrawal hole for the probe becomes closed by means of a check valve which, possibly may be included in the sampling apparatus. Fluid samples taken isokenitically by the sampling apparatus are analyzed in order to determine corresponding fraction values. The values determined from the corresponding fraction values can be used as prescribed (reference) values as a base for any necessary calibration of the electronic fractions meters.

3 Claims, 2 Drawing Sheets

USE OF A SAMPLING APPARATUS FOR CALIBRATING ELECTRONIC MASS/FLOW FRACTION METERS IN A PIPELINE

BACKGROUND

The invention relates to a use of a sampling apparatus shaped with the aim of taking samples isokinetically from a mass flow in the form of a two- or multi-phase fluid in a pipeline assigned i.a. electronic measuring apparatus. The sampling apparatus is meant to be coupled continuously to the pipeline, either at the seabed or at the well head on a platform.

Prior art techniques comprise test separators separating the fractions (oil, gas, water, sand, condensate) of the multi-phase fluid. The amount of production for each fraction per unit of time is measured. This must be done regularly at each well.

Such test separators are heavy, and they are expensive in purchase and use.

In order to reduce the costs and simultanelously to enable a continuous testing of the wells in respect of the composition of the multi-phase fluid, it has been of great interest to find new technological solutions. Mass flow measuring has resulted in the use of electronic fraction measuring apparatus and metering appliances for measuring temperature and pressure in a multi-phase fluid flowing in a pipeline. Mass flow or fraction metering appliances enable electronic metering of the amount of gas, oil, sand and water flowing past a certain pipe cross section per unit of time. This electronic multi-phase measuring has experienced great confidence. Mass flow or fraction meters exist in various embodiments and designs, and may be based on the measurement of electrical voltages in the various fractions.

However, the electronic fraction meters that have been in use up to now have not been sufficiently accurate. They are adapted to transmit signals to a computer displaying the measuring results, which can differ rather significantly from the actual values. The corresponding measuring values achieved by means of the test separator may possibly be used as prescribed values when the electronic fraction meters are calibrated, but one desires to eliminate the test separators because of their weight, high price and substantial operational costs.

The object of the present invention has been to eliminate the use of test separators and, thus, to relieve the platform, obtaining significant cost savings; simultaneously enabling the provision, at all times, of accurate measuring results well suited as prescribed values for the calibration of said electronic mass flow/fraction meters.

By means of a sampling apparatus, known per se, possibly modified, adapted for isokinetic sampling, a probe is inserted into the mass flow within a pipeline, said probe, preferably, having two oppositely directed orifice plates, in order to bring out one single sample or a sample taken in co-current and a sample taken counter-currently. The sample taken isokinetically, is analyzed, e.g., in a spectrograph. The measuring values obtained are very close to the actual values and are, thus, well suited as prescribed values constituting a base for calibrating calibratable electronic mass flow/fraction meters. Corrections may be placed in the software of the processor unit of the electronic measuring instruments. The sampling apparatus which, e.g., may be of the kind as described and shown in Norwegian patent specification No. 173,468, enables isokinetic sampling. This apparatus comprises an actuator coupled to a check valve which, in turn, is coupled to the fluid-carrying pipeline through a through hole in the pipe wall. When the check valve occupies an open position, the actuator can place a probe into said hole, laterally of the longitudinal direction of the pipeline. The probe may have one or two diametrally opposite orifice plates, which can be moved across substantially the entire inner span of the pipeline, in order to take out fluid samples from at least the main part of the cross-sectional area of the fluid flow.

If the apparatus is placed at the seabed, this/these sample (s) may be delivered on board the platform through a pipeline for analysis.

The sampling apparatus is adapted to be permanently mounted to the pipeline on the seabed or on the well head of a platform, and makes a test separator completely superfluous.

A sampling apparatus used in accordance with the present invention serves primarily to provide accurate measuring results associated with the amounts, expressed in percentages, of the respective fractions for use as prescribed values for the calibration of the fraction meters, but enables secondarily the achievement of other measuring results, such as pressure, temperature, etc.

In accordance with the invention, there has been provided an independent measuring technique based on the use of a sampling apparatus in order to improve measuring results in quality, and to take samples. The sampling apparatus may be placed upstream or downstream in relation to the calibratable electronic fraction meters.

It may be an advantage to use the sampling apparatus in combination with a per se known, possibly modified mixing apparatus e.g., of the kind shown and described in Norwegian patent specification No. 174,015. Such a mixing apparatus would be mounted to said pipeline upstream in relation to the sampling apparatus and comprises a throttle body which is displaceable laterally of the longitudinal direction of the pipeline and which in operative position registers with the inner cross-sectional area of pipeline. The throttle body has converging channels, tapering in the direction of flow, and the longitudinal axes thereof meet in an imaginary, so called "focal point" (crossing point), and serve to mix the various fractions of the multi-phase fluid. Without such a mixing, one could risk that a liquid jacket immediately adjacent the inner wall surface of the pipeline would not be included in the sample. This mixing apparatus, which possibly could be deleted, has hydraulic actuators; the control lines thereof may be included in a so called umbilical, or they may be operated from, e.g., a remote control vehicle.

Isokinetic sampling gives accurate samples for the determination of produced amounts of oil, of gas, of water, of formation sand and of condensate per unit of time, as well as temperature and pressure at the measuring point on the pipeline. If the sampling apparatus, possibly together with the mixing apparatus, are placed on the well head on the platform, the apparatus may be controlled from a control room and operated manually.

BRIEF DESCRIPTION OF THE DRAWING

A non-restricting example of a possible embodiment of the invention is illustrated in the drawings, the scale thereof not necessarily showing the correct proportions between the various dimensions, and wherein.

DETAILED DESCRIPTION

Figure 1:
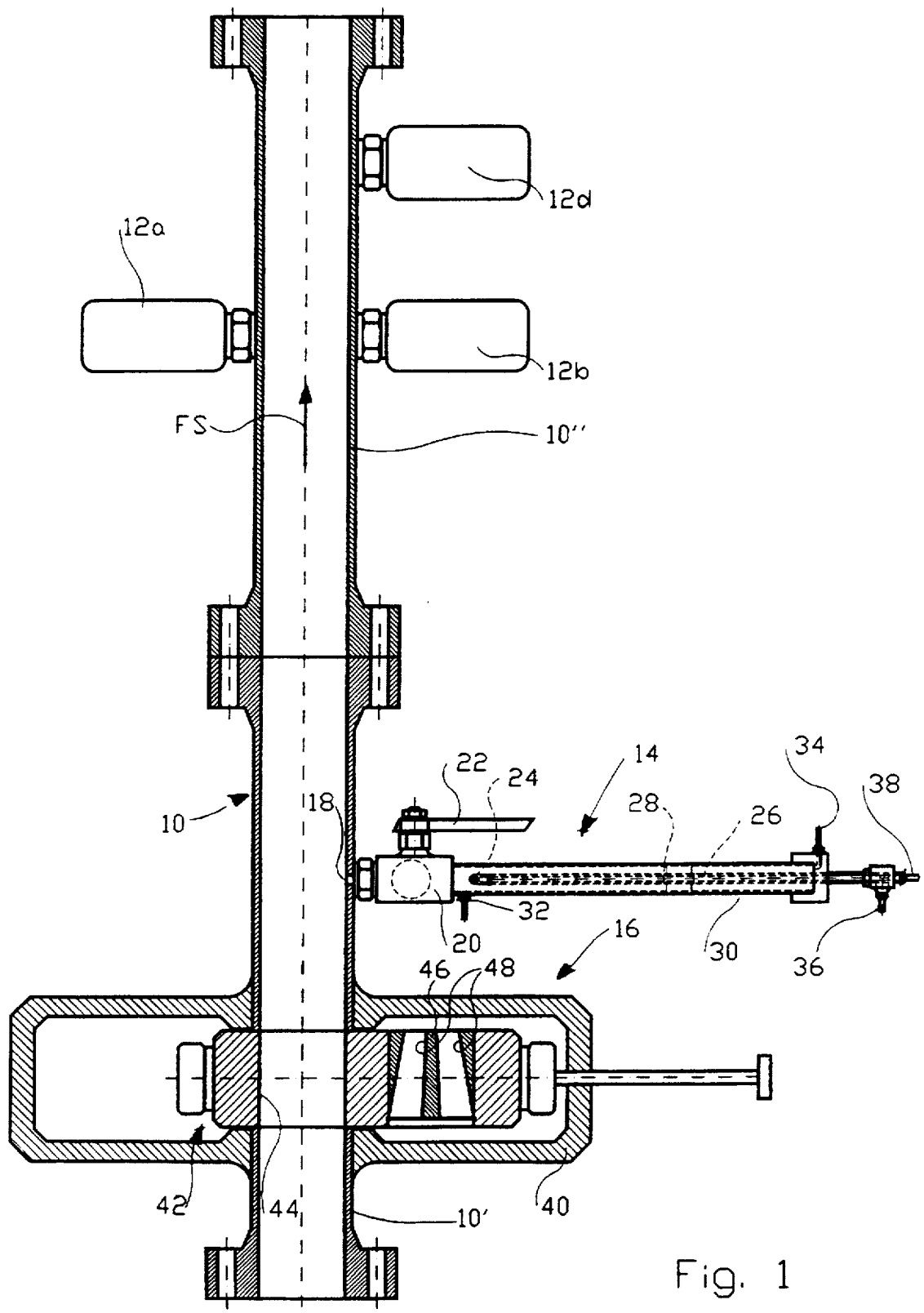
FIG. 1 shows a pipeline carrying a multi-phase fluid and provided with electronic mass flow meters respectively fraction meters, a sampling apparatus and a mixing apparatus, the latter being placed upstream in relation to the sampling apparatus, and wherein the sampling apparatus and the mixing apparatus are shown in non-operative positions of readiness, where they do not interfere with the flow cross-section of the pipeline.

In the figures of the drawings, a vertically directed pipeline 10 is shown, but the pipeline might have any orientation whatsoever, and may e.g. consist of a production tube string jointed together of flanged pipe sections 10 and 10". Normally, the pipe sections 10'–10" would have a substantially larger length in relation to the diameter shown, and the scale of the figures is not true, neither for pipeline nor for connected equipment.

The pipeline 10 serves to carry a two- or multi-phase fluid which through inherent speed, pressure and temperature flows as a mass flow through the pipeline 10. The liquid phase (oil) of the fluid may be imagined to appear as a peripherical "jacket" closest to the inner surface of the pipe line 10, while the gaseous fraction flows centrally. Further fractions may consist of water/condensate and formation sand.

In the embodiment shown,the pipeline 10 is assigned, e.g., three calibratable, electronic mass flow/fraction meters 12a, 12b and 12d, the task and cooperation thereof with a central computer have been explained in the introduction. As such electronic meters appear in many embodiments and designs and represent well known technique, they will not be further described in this connection. Thus, the object of the invention is to provide accurate measuring results, which may form the basis for prescribed values to be used when calibrating the electronic mass flow/fraction meters 12a, 12b, and 12d. The utilization of the more accurate measuring results as prescribed values and the further utilization of the latter upon the calibration of the fraction meters may be effected through feeding correction factors to the software of the processor unit of the electronic measuring instruments, and represent, moreover, elementary data technique.

Thus, the starting point for the present invention is a pipeline carrying a flowing multi-phase fluid and which is provided with electronic mass flow/fraction meters which are calibratable.

To this end, the present invention consist in the use of a sampling apparatus, generally denoted with reference numeral 14, designed, shaped and adapted to take fluid samples isokinetically. This sampling apparatus, especially in connection with an upstream mixing apparatus 16, is capable of taking very accurate samples which, upon analysis, will give better measuring values than the electronic fraction meters.

Figure 2:
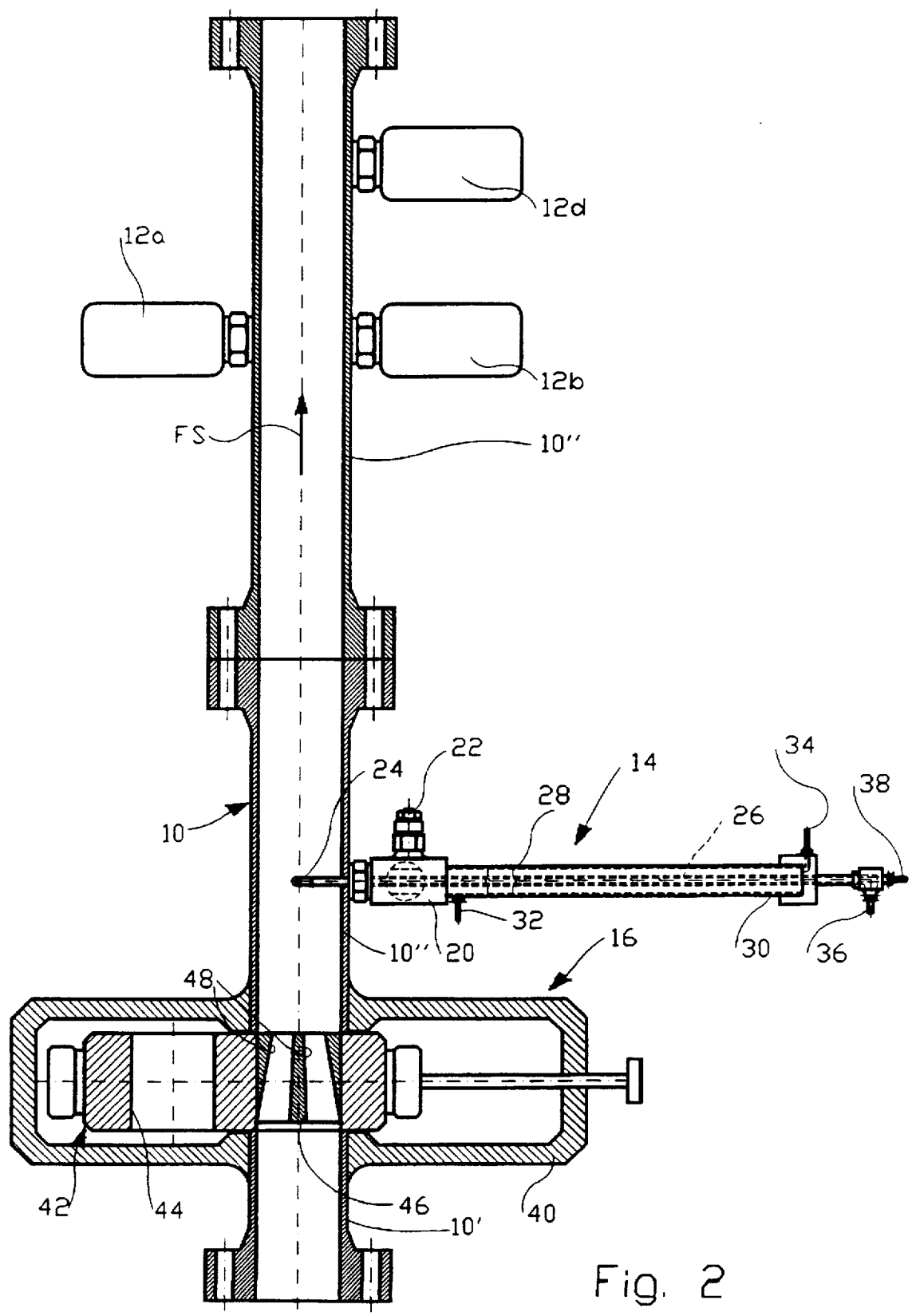
FIG. 2 shows the same as FIG. 1, but here the sampling apparatus and the mixing apparatus are shown in the operative positions thereof, where they engage physically into the flow cross-section of the pipeline.

The sampling apparatus is adapted to be coupled to a measuring point constituted by a through hole 18 in the pipe wall, where a connection pipe stub has been formed, to which a check valve 20 having an operating handle 22 has been coupled. Closed valve 20 closes the hole 18, while open valve, FIG. 2, allows the passage of a linearly displaceable probe 24.

The probe 24 can be operated by means of a to and fro displaceable piston rod incorporated in a piston cylinder or a corresponding actuator, said piston rod—in the case comprising two orifice plates—consists of two concentrical pipes, in which fluid samples from the two orifice plates are accommodated, the samples being conveyed further separately. Connection hoses between the apparatus 14 and the surface (if the apparatus not already has been mounted on the well head on the platform) may, e.g., be included in the umbilical. When the apparatus 14 has been placed submarinely, permanently coupled to the pipeline 10, one may use a remote control vehicle to operate the apparatus. For a further, more detailed description of this sampling apparatus 14, reference is made to the previously mentioned NO-173,468. Alternatively, other similar sampling apparatus may, of course, be used, provided they are designed, shaped and adapted to take fluid samples isokinetically. However, it should be added that said piston rod 26 carries a piston 28 which is displaceable in a cylinder 30 and influenced by means of pressurized fluid through hydraulic hoses 32, 34. Hoses 36, 38 for the further transfer of co-current sample and counter-current sample are indicated through short (cut) hose pieces.

As mentioned, the sampling apparatus 14 is assigned a mixing apparatus 16 coupled to the pipeline 10. The mixing apparatus 16 may be of any embodiment or design, known per se. The housing of the mixing apparatus 16 is constituted by an annular valve housing 40 designed and shaped for fluid-tight connection around the pipeline 10 in the area of diametrally opposite circular apertures therein. The valve housing 40 contains a linearly displaceable valve body 42 having a lateral, through-going bore 44 having the same diameter and shape as the bore of the pipeline 10 and which can be brought to register accurately with the same in the inoperative position of readiness of the mixing apparatus 16, FIG. 1. 46 denotes the virtual mixing body in the form of an insert which, possibly, could be replaced and substituted by another insert adapted to give a different mixing pattern. In the embodiment shown, the mixing body 46 is formed with two channels 48 converging and tapering in the direction FS of the fluid flow, and the axes thereof meet in an imaginary "focal point" (crossing point). The positioning of the probe 24 in relation to this "focal point" (crossing point) could influence the accuracy of the measuring results. The channels 48 cause a certain throttling of the fluid flow and, thus, mix the various fractions, such that the probe 24 takes out a mixed fluid. The mixing body 46 is shown in operative position in FIG. 2.

The term "pipeline" should be interpreted in the general sense. A pipeline wherein a multi-phase fluid is flowing may have functional enlargements and lateral extensions, in which fraction meters, sampling and mixing apparatus may be disposed.

I claim:

1. A method of isokenitically sampling fluid flowing within a pipe and calibrating mass flow/fraction meters comprising the steps of:

opening a check valve disposed adjacent to a through hole;

inserting an isokenitic sampling probe through the through hole, said probe having at least one orifice plate;

taking a sample of fluid within the pipe with the probe;

withdrawing the probe from the check valve and the through hole;

closing the check valve;

analyzing the sample; and calibrating a mass flow/fraction meter attached to the pipe based on results of the sample analysis.

2. The method of claim 1 further comprising the step of mixing the fluid within the pipe upstream of the through hole.

3. The method of claim 2 further comprising the steps of:

inserting a mixing body into the pipe a suitable distance upstream of the through hole before the probe is sampling the fluid; and removing the mixing body from the pipe.

* * * * *